United States Patent [19]

Lorenz et al.

[11] 4,218,392
[45] Aug. 19, 1980

[54] TWO-STEP METHOD OF MAKING COPOLYMERIZABLE, ULTRAVIOLET LIGHT ABSORBER 2-CYANO-3,3-DIPHENYLACRYLOXY) ALKYLENE ACRYLIC ACID ESTERS

[75] Inventors: Donald H. Lorenz, Basking Ridge; Bruce A. Gruber, Bloomingdale, both of N.J.

[73] Assignee: GAF Corporation, New York, N.Y.

[21] Appl. No.: 39,561

[22] Filed: May 16, 1979

Related U.S. Application Data

[63] Continuation-in-part of Ser. No. 6,787, Jan. 26, 1979, Pat. No. 4,178,303.

[51] Int. Cl.$^2$ .................................................. C07C 121/70
[52] U.S. Cl. ........................ 260/465 D; 260/45.85 A; 260/465.4
[58] Field of Search ........................ 260/465 D, 465.4

[56] References Cited

U.S. PATENT DOCUMENTS

| | | | |
|---|---|---|---|
| 3,644,466 | 2/1972 | Strobel et al. | 260/465 D |
| 3,993,684 | 11/1976 | Dunnavant et al. | 260/465 D X |

*Primary Examiner*—Dolph H. Torrence
*Attorney, Agent, or Firm*—Walter C. Kehm; Walter Katz

[57] ABSTRACT

This invention relates to a method of making in high yield light absorber compounds which are (2-cyano-3,3-diphenylacryloxy) alkylene acrylic acid esters having the formula:

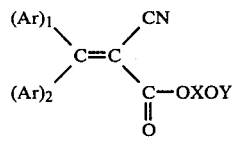

where
(Ar)$_1$ and (Ar)$_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl and naphthyl;

X is alkylene, C$_2$–C$_{17}$, unsubstituted or substituted with halo, cyano, alkyl C$_1$–C$_6$ alkoxy C$_1$–C$_6$, alkoxyalkyl C$_1$–C$_6$, or alkoxyalkyleneoxy C$_1$–C$_6$; and Y is copolymerizable radical selected from acryloyl C$_3$–C$_{12}$ alkylacryloyl C$_3$–C$_{12}$, acryloxyalkyl C$_3$–C$_{12}$, acryloxyhydroxyalkyl and alkylacryloxyhydroxyalkyl C$_3$–C$_{12}$.

The method comprises:
(a) esterifying a hydroxyalkylene cyanoacetate with an acryloylhalide or acrylic acid to form a (2-acryloxyalkyl) 2-cyanoacetate intermediate, and,
(b) condensing the intermediate directly with a benzophenone to provide the desired product.

7 Claims, No Drawings

TWO-STEP METHOD OF MAKING COPOLYMERIZABLE, ULTRAVIOLET LIGHT ABSORBER 2-CYANO-3,3-DIPHENYLACRYLOXY) ALKYLENE ACRYLIC ACID ESTERS

BACKGROUND OF THE INVENTION

1. Field of the Invention

This invention relates to a method of making ultraviolet light absorber compounds and, more particularly, to a two-step method of preparing 2cyano-3,3-diphenylacryloxy acrylic acid ester compounds in high yield. The compounds herein copolymerize with vinyl monomers to produce polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Related Patent Applications

Copending patent application Ser. No. 006,787, filed Jan. 26, 1979, now U.S. Pat. No. 4,178,303 by the same applicants as herein, and assigned to the same assignee, describes novel copolymerizable ultraviolet light absorber compounds which are substantially free of the disadvantages of the prior art. This application is a continuation-in-part of said copending patent application.

SUMMARY OF THE INVENTION

What is provided herein is a two-step method of making in high yield copolymerizable ultraviolet light absorber compounds which are (2-cyano-3,3diphenylacryloxy) alkylene acrylic acid esters of the formula:

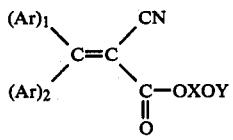

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, $C_2$–$C_{17}$, unsubstituted or substituted with halo, cyano, alkyl $C_1$–$C_6$, alkoxy $C_1$–$C_6$, alkoxyalkyl $C_1$–$C_6$ or alkoxyalkyleneoxy $C_1$–$C_6$; and, Y is copolymerizable radical selected from acryloyl $C_3$–$C_{12}$, alkylacryloyl $C_3$–$C_{12}$, acryloxyalkyl $C_3$–$C_{12}$ acryloxyhydroxyalkyl, and alkylacryloxyhydroxyalkyl $C_3$–$C_{12}$.

The method comprises:

(a) esterifying hydroxyalkylene cyanoacetate with an acryloyl halide or acrylic acid to form a (2-acryloxyalkyl)2-cyanoacetate intermediate, and, (b) condensing the intermediate directly with a benzophenone to provide the desired product.

DETAILED DESCRIPTION OF THE INVENTION

Suitable $(Ar)_1$ and $(Ar)_2$ groups are given in U.S. Pat. No. 3,644,466, including representative starting benzophenone compounds. In the best mode of the invention both $(Ar)_1$ and $(Ar)_2$ are phenyl.

The X groups are unsubstituted or substituted alkylene radicals, $C_2$–$C_{17}$. The preferred groups are unsubstituted lower alkylene, $C_2$–$C_6$, which are derived synthetically from ethylene glycol, propylene glycol, butanediol, and the like. The best mode is represented by —$CH_2$—$CH_2$—.

The Y radical is copolymerizable with vinyl monomers so that the ultraviolet absorber becomes an integral part of the polymer. Suitable Y groups are derived from acryloyl $C_3$–$C_{12}$, alkylacryloyl $C_3$–$C_{12}$, acryloxyalkyl $C_3$–$C_{12}$, acryloylhydroxyalkyl and alkylacryloxyhydroxyalkyl, $C_3$–$C_{12}$. The preferred groups are acryloyl, methacryloyl, glycidyl acryloyl and glycidyl methacryloxy. The best mode is represented by acryloyl or methacryloyl.

The compounds of the invention contain ultraviolet light absorber and copolymerizable portions in the same molecule. These portions are effectively separated by the X radical so that each can perform its own function without interference from the other. Therefore, the absorber portion does not inhibit the copolymerization, and the Y radical does not affect the light absorbing properties of the molecule.

In step (a) of the two-step method of the invention, a hydroxyalkyl cyanoacetate is reacted with an acryloyl halide or acrylic acid to form a 2-(acryloxyalkyl) 2-cyanoacetate intermediate. Then the intermediate is condensed directly in step (b) with a benzophenone Knoevenagel reaction to form the desired compounds, as follows:

METHOD OF INVENTION

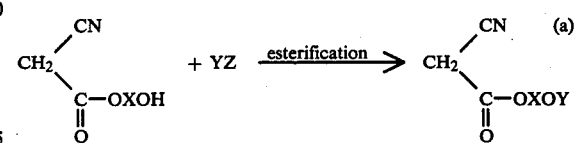

where YZ is an acryloyl halide or acrylic acid, and X and Y are as defined above.

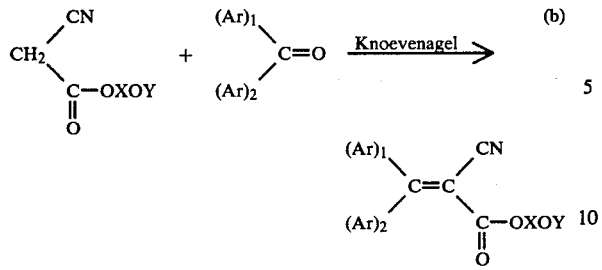

Typical X groups are —CH₂CH₂, —CH₂CH₂CH₂—CH₂CH₂CH₂CH₂—, and the like.

Representative Y groups are $$-\underset{\underset{O}{\|}}{C}-CH=CH_2 \text{ (acryloyl)}, \quad -\underset{\underset{O}{\|}}{C}-C(CH_3)=CH_2 \text{ (methacryloyl)},$$

$$-CH_2-CH(OH)CH_2O\underset{\underset{O}{\|}}{C}CH=CH_2$$

(3-acryloyxy-2-hydroxypropyl), and $$-CH_2CH(OH)CH_2O\underset{\underset{O}{\|}}{C}C(CH_3)=CH_2$$

(3-methacryloxy-2-hydroxypropyl).

Step (a) involves esterification of hydroxyalkyl cyanoacetate with a reactive acryloyl compound, such as an acryloyl halide e.g. acryloyl chloride or acryloyl bromide. The reaction is carried out in an inert solvent, suitable any aromatic or aliphatic hydrocarbon or halogenated hydrocarbon, such as toluene, benzene, chloroform or ethylene dichloride, or in acetone, at a suitable temperature, generally ranging from room temperature to the reflux temperature of the solvent, e.g. if chloroform, at about 61° C., and in the presence of a base, such as sodium bicarbonate, to absorb the acid by-product of the reaction. Suitably the molar ratios of the reactants are controlled to provide at least a 1:1 molar ratio of the acryloyl halide to the hydroxyalkyl cyanoacetate. Preferably an excess of the acryloyl compound is used. The reaction is run for about 1–5 hours at the reflux temperature.

The yield of the intermediate in step (a) is about 80–90%.

An acrylic acid may be used in place of the acryloyl halide in step (a). In this embodiment, water is distilled out of the reaction mixture as an azeotrope with the solvent. Preferably, an inhibitor, such as phenothiazine or methoxyphenol, is included in the reaction mixture in an amount of about 200-1000 ppm to prevent polymerization of the acrylic acid reactant. The reaction with acrylic acid generally is run at a somewhat higher temperature than with the acryloyl halide, usually at about 80°-110° C., for about 10 to about 20 hours. The yields are about 60–70%.

Step (b) in the process involves direct Knoevenagel reaction is generally run in the presence of a solvent, such as benzene, toluene, or ethylenedichloride, under reflux, usually at a temperature between 80° and 100° C. for about 24 hours. The reaction preferably proceeds in a nitrogen atmosphere and in the presence of glacial acetic acid and ammonium acetate as a catalyst. Conventional washings of the product with water and saturated bicarbonate solution are done prior to the drying, removing the solvent, and recovering the product.

The compounds of the invention may be copolymerized, for example, with a urethane oligomer, by radiation curing, to provide useful polymeric coatings.

The following examples will describe the invention with more particularity.

EXAMPLE 1

2-(2-Cyano-3,3-Diphenylacryloxy) Ethyl Acrylate

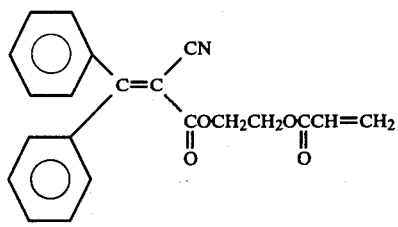

(a) Acryloxyethyl 2-Cyanoacetate

Cyanoacetic acid was esterified with ethylene glycol according to U.S. Pat. No. 3,644,466 (Co. 7–8, Ex. 3) to give (2-hydroxyethyl)2-cyanoacetate in 74% yield.

Into a flask fitted with a mechanical stirrer and a reflux condenser is charged 1 l. of methylene chloride 129 g. (1 mole), (2-hydroxyethyl)2-cyanoacetate 118 g. (1.3 moles), acryloyl chloride and 179 g. potassium carbonate. The reaction mixture was heated at reflux (41° C.) for 2 hours, diluted with 1 l. of water and neutralized with solid potassium carbonate. The organic layer then was separated, dried and evaporated leaving 128 g. (70%) of (2-acryloxyethyl)2-cyanoacetate, which was stabilized with 50 ppm of hydroquinone.

(b) In a round bottom flask equipped with a mechanical stirrer, a thermometer, and a Dean-Stark water trap fitted with a reflux condenser was charged 270 ml. toluene, 182 g. (1 mole) of benzophenone, 183 g. (1 mole) of 2-acryloxyethyl 2-cyanoacetate, 26 mg. of phenothiazine, 50 ml. of glacial acetic acid, and 20 g. of ammonium acetate. The solution then was heated at reflux (110° C.) for 16 hours. After cooling, the reaction solution was washed with 300 ml. of water and the organic layer was separated and dried. The toluene solvent was evaporated leaving an amber oil which was predominantly the product compound.

EXAMPLE 2

The compound of Example 1 was prepared using acrylic acid instead of acryloyl chloride in Step (a) of Example 1 to provide the desired intermediate.

(a) A charge of 118 g. (1 mole) of (2-hydroxyethyl) 2-cyanoacetate in 1.5 l. of toluene was heated at reflux (110° C.) to remove residual water and the solution was cooled to 30° C. Then 96 g. (1.3 moles) of acrylic acid, 5 g. of p-toluene sulfonic acid and 350 mg. of phenothiazine was added and the solution was heated at reflux for 16 hours. The reaction mixture then was cooled to room temperature and 1 l. of water was added and the solution was neutralized with solid potassium carbonate. The organic layer then was dried and evaporated to yield 328 g. (80% yield, about 75% purity) of an amber oil of the intermediate compound.

(b) The intermediate of Step (a) was converted to the desired product as in example 1.

EXAMPLE 3

2-(2-Cyano-3,3-Diphenylacryloxy) Ethyl Methacrylate

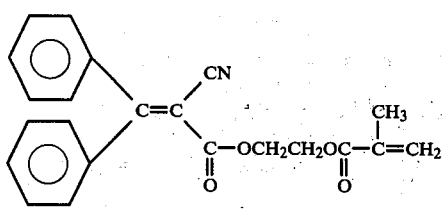

Using an equivalent amount of methacryloyl chloride in place of acryloyl chloride in Step (a) of Example 1, the desired ethyl methacrylate compond is obtained in comparable yield.

EXAMPLE 4

3-(2-Cyano-3,3-Diphenylacryloyl) Propyl Methacrylate

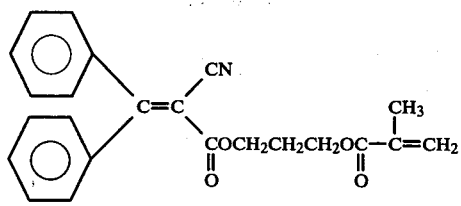

Using an equivalent amount of propylene glycol in place of ethylene glycol in Example 3, there is produced the desired propyl methacrylate compound in comparable yield.

EXAMPLE 5

4-(2-Cyano-3,3-Diphenylacryloyl) Butyl Acrylate

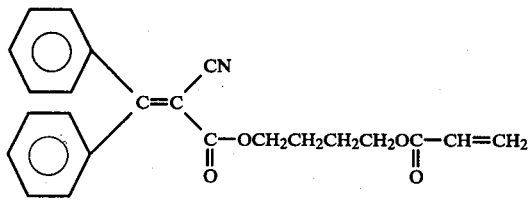

By substituting 1,4-butanediol in place of ethylene glycol in Example 1, there is produced the corresponding butyl acrylate.

EXAMPLE 6

2-Hydroxy-3-(2-Cyano-3,3-Diphenyl acryloxy) Ethoxy Propyl Acrylate

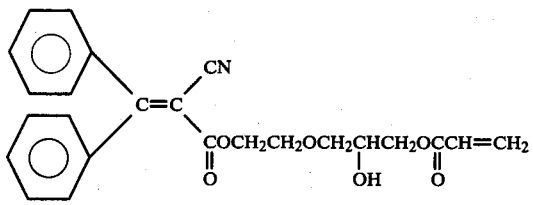

The procedure of Example 1 is followed except for (a) as follows:

Into a round bottom flask is charged 29.3 g. (0.1 mole) of 2-hydroxyethyl 2-cyano-3,3-diphenylacrylate, 21.3 g. (0.15 mole) glycidyl acrylate and 0. 27 g. (0.0025 mole) tetramethylammonium chloride. The mixture was heated at 70°–90° for 5 hours. Thereafter excess glycidyl acrylate was removed by vacuum distillation. The remaining amber oil was the desired ethoxy propyl acrylate product.

EXAMPLE 7

2-Hydroxy-3- (2-Cyano-3,3-Diphenylacryloxy) Ethoxy Propyl Methacrylate

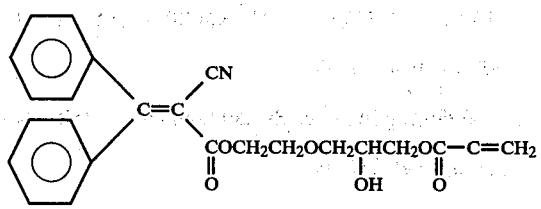

Using glycidyl methacrylate in place of glycidyl acrylate in Example 6 gives corresponding methacrylate compound.

While certain preferred embodiments of the present invention invention have been illustrated by way of specific example it is to be understood that the present in no way to be deemed as limited thereto but should be construed as broadly as all for any equivalents thereof.

What is claimed is:

1. A method of making copolymerizable ultraviolet light absorber (2-cyano-3,3-diphenylacryloxy) alkylene acrylic acid esters in high yield having the formula:

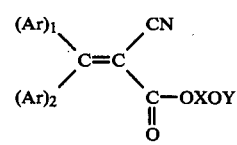

where (Ar)$_1$ and (Ar)$_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, $C_2$–$C_{17}$, unsubstituted or substituted with halo, cyano, alkyl $C_1$–$C_6$, alkoxy $C_1$–$C_6$, alkoxyalkyl $C_1$–$C_6$, or alkoxyalkyleneoxy $C_1$–$C_6$; and, Y is copolymerizable radical selected from acryloyl $C_3$–$C_{12}$, alkylacryloyl $C_3$–$C_{12}$, acryloxyalkyl $C_3$–$C_{12}$, acryloxyhydroxyalkyl and alkylacryloxyhydroxyalkyl $C_3$–$C_{12}$, which comprises the steps of:

(a) esterifying a hydroxyalkylene cyanoacetate having the formula:

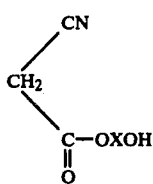

where X is as defined above, with an acryloyl halide or acrylic acid having the formula YZ, where Y is as defined above and Z is a halide or hydroxyl group to form a (2-acryloxyalkyl) 2-cyanoacetate intermediate, and, (b) condensing the intermediate with a benzophenone having the formula:

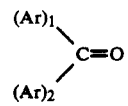

where $(Ar)_1$ and $(Ar)_2$ are as defined above, to form the desired compound.

2. A method according to claim 1 in which both $(Ar)_1$ and $(Ar)_2$ are phenyl.

3. A method according to claim 1 in which X is alkylene, $C_2$–$C_6$.

4. A method according to claim 1 in which Y is acryloyl, methacryloyl, 3-acryloxy-2-hydroxypropyl or 3-methacryloxy-2-hydroxypropyl.

5. A method according to claim 1 in which both $(Ar)_1$ and $(Ar)_2$ are phenyl, x is alkylene, $C_2$–$C_6$ and Y is acryloyl, methacryloyl, 3-acryoxy-2-hydroxypropyl or 3-methacryloxy-2-hydroxypropyl.

6. A method according to claim 1 in which YZ is an acryloyl halide.

7. A method according to claim 1 in which YZ is an acrylic acid.

* * * * *